United States Patent [19]

Hilton

[11] 4,430,995

[45] Feb. 14, 1984

[54] POWER ASSISTED AIR-PURIFYING RESPIRATORS

[76] Inventor: Joseph R. Hilton, 2 Goldfinch Gardens, Guildford, Surrey GU4 7DN, England

[21] Appl. No.: 381,632

[22] Filed: May 24, 1982

[30] Foreign Application Priority Data

May 29, 1981 [GB] United Kingdom ................ 8116424

[51] Int. Cl.³ .............................................. A62B 7/10
[52] U.S. Cl. .......................... 128/204.21; 128/204.28; 128/205.12; 417/45
[58] Field of Search ....................... 128/204.21, 204.23, 128/205.12, 205.13, 205.16, 205.18, 204.28, 204.18; 417/45

[56] References Cited

U.S. PATENT DOCUMENTS

| | | | |
|---|---|---|---|
| 855,046 | 5/1907 | Cousans | 417/45 |
| 1,308,599 | 7/1919 | Luchs | 128/204.28 |
| 2,830,580 | 4/1958 | Saklad et al. | 128/204.23 |
| 3,501,899 | 3/1970 | Allen | 417/45 |
| 3,863,630 | 2/1975 | Cavallo | 128/204.21 |
| 4,233,972 | 11/1980 | Hauff et al. | 128/205.12 |
| 4,364,384 | 12/1982 | Warncke et al. | 128/205.16 |

*Primary Examiner*—Henry J. Recla

*Attorney, Agent, or Firm*—Laubscher, Philpitt & Laubscher

[57] ABSTRACT

The present invention relates to an improved air-purifying device for respirators of the positive pressure type.

The device comprises an expandable chamber having an outlet for connection to a facepiece, for example, a face mask, and an inlet connected to a pump for drawing ambient air into the device through a filter and pumping it into the chamber. In use, the wearer of the face mask draws air from the chamber and that air is replenished by operation of the pump.

Apparatus is provided for sensing the degree of expansion of the expandable chamber and is coupled with a device for varying the power supplied to the pump so that the pump means supplies only sufficient filtered air to maintain the chamber inflated. A bias is provided on the chamber, advantageously coupled with the sensing apparatus for maintaining a positive pressure in the chamber.

An air-purifying device allows close control of the amount of air passing through the respirator so as to substantially reduce the amount of air which is filtered but unbreathed to extend the life of the filter.

11 Claims, 4 Drawing Figures

POWER ASSISTED AIR-PURIFYING RESPIRATORS

FIELD OF THE INVENTION

The present invention relates to improvements in power assisted air-purifying respirators.

BRIEF DESCRIPTION OF THE PRIOR ART

The use of power assisted respirators in atmospheres contaminated by dust and other particulate hazards is well known. Usually such respirators comprise a pump unit including a battery-powered motor driving a fan which draws contaminated air through a filter system and delivers it to a facepiece which may be a full-face mask or included in a helmet or hood. The advantages of power assisted respirators over non-powered respirators in which a filter cartridge is mounted directly on a full-face mask, are the ease of breathing and, in most cases, the increased protection afforded to the wearer since air is supplied to the facepiece at a slight positive pressure. Additionally filters of high efficiency having a correspondingly higher resistance to flow can be used, which would otherwise impose a physiologically unacceptable strain on the lungs of the wearer.

Normally the air flow provided by the pump unit is reasonably constant but is greatly in excess of the inspiratory requirements of the wearer. U.K. and European standards require a minimum flow of 120 liters per minute for four hours in order to sustain a degree of positive pressure within the facepiece even at peak inhalation rate, for example as set out in British standard 4558; 1970 Positive Pressure Powered Dust Respirators, Section 5, paragraph 5.1. In the United States the relevant standard 30CFR part II published by the National Institute of Occupational Safety and Health (NIOSH) requires a minimum flow of 113 liters per minute for tight fitting full-face masks and a 170 liters per minute for helmets and hoods.

It will be seen that this constant flow roughly equates to the instantaneous peak inspiratory rate of a man working moderately hard having a minute volume of 40 liters per minute (20 respirations per minute each having a 2 liter tidal volume). Assuming a sinusoidal breathing pattern, it can be shown that peak rate is equal to $\pi \times$ (minute volume). For a man working harder than 40 liters per minute there would be inspiratory peaks of negative pressure within the facepiece but these would be transitory and such exertion cannot be maintained for a four hour, much less an eight hour, period.

In conventional power assisted air-purifying respirators it follows that for a greater part of the wearing period, the volume of ambient air being filtered and delivered to the wearer is many times the actual requirement for breathing purposes and the major part of the air goes to waste through the exhale valve, filtered but unbreathed. This leads to a much more rapid usage of the filter than is the case with unpowered respirators, and is also wasteful of motor and battery power. Nonetheless it is tolerated in the case of dust and other particulate hazards because of the advantages outlined above and because it is possible to design a particulate filter system of not unreasonable size and cost to cope with the increased particulate burden of constant flow.

The situation where such respirators are used against gases and vapors is very different. Gas and vapour contaminants are usually eliminated by filters advantageously mounted in canisters, and which are attached to a full-face mask either directly or by a short length of flexible corrugated hose so that the wearer draws only sufficient air through the canisters as he requires for breathing. Usually the canisters contain granulated activated charcoal, silica gel, molecular sieve material or similar material through which the contaminated ambient air is drawn by lung power, the contaminants being adsorbed on the surface of the sorbant and retained there. By 'doping' of the adsorbent material the canister can be given a degree of specificity against particular contaminants. Combination canisters for filtering both particulate and gas/vapour contaminants are also available. The duration of these canisters is necessarily limited by the volume of the adsorbent in the canister, and this is particularly true of those canisters intended to be screwed directly into a face mask, and is significantly less than particulate material filters. Although these gas/vapour canister filters form a readily available and desirable source of filters for attachment to power assisted respirators, their useful lifetime is very significantly reduced because of the high proportion of the filtered air which is wasted. This proportion may be as high as 80%.

SUMMARY OF THE INVENTION

According to the present invention there is provided an air-purifying device for attachment to a facepiece of the positive pressure type for providing purified air to the wearer of the facepiece, the air-purifying device comprising pump means for pumping air having inlet means and outlet means, means for removing contaminants in the air and connected to the pump inlet means, an expandable chamber having an inlet in communication with the pump outlet means and an outlet for connection to the facepiece, sensing means for sensing the degree of expansion of the expandable chamber, and means for varying the power supplied to the pump means in dependence on the state of expansion of the expandable chamber.

The pump means may comprise a motor driving a fan having an inlet connected to one or more air inlets with each of which means for removing contaminants in the air is connected. The removing means may comprise a canister removably mounted on the or each inlet and filled with a material appropriate to adsorb or otherwise filter out the or each contaminant concerned, for example gas and/or vapour and/or dust.

The expandable chamber may comprise a bag which is generally cylindrical with a convoluted cylindrical wall and may be biased towards its collapsed condition for maintaining a positive pressure in the chamber. The means for sensing the degree of inflation of the expandable chamber may comprise an arm which bears against a wall of the chamber which wall moves in dependence on the state of expansion of the chamber and the arm may be connected to means which is included in the power supply circuit to the motor for varying the voltage supply to the motor or which may include switch means for disconnecting the motor from and connecting the motor to its power supply.

Where the voltage is varied, the chamber may be arranged to be maintained substantially fully inflated, the motor is disconnected from its power supply when the chamber is substantially fully inflated and reconnected when the chamber reaches a predetermined state of partial deflation.

The present invention also relates to a respirator comprising a facepiece connected to an air-purifying device as set out above.

The facepiece may comprise a partial or full-face mask for covering at least the nose and mouth of the wearer or may be included in a helmet or hood covering the head of the wearer.

BRIEF DESCRIPTION OF THE DRAWINGS

An embodiment of the invention will now be described, by way of example only, with reference to the accompanying drawings.

In the drawings.

DETAILED DESCRIPTION

Figure 1:
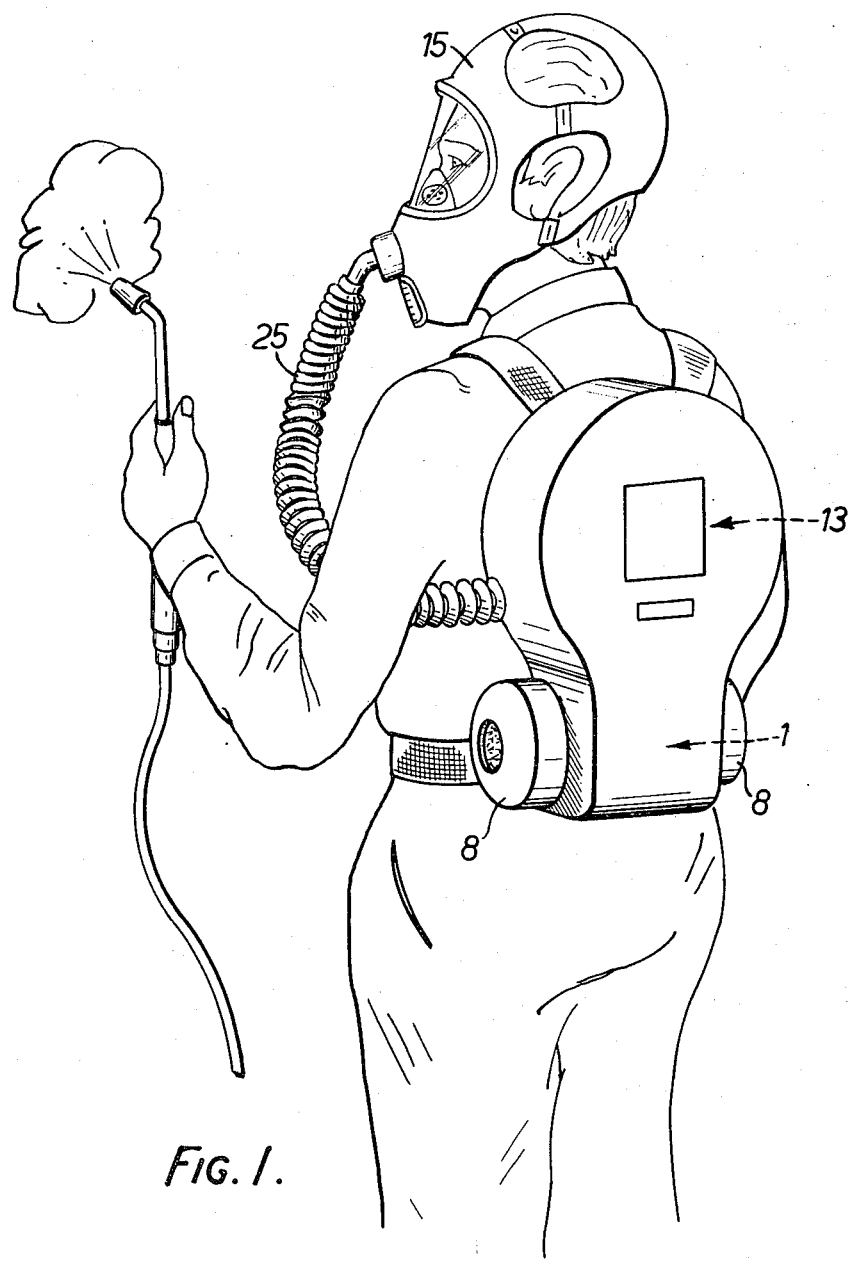
FIG. 1 is a perspective view of an embodiment of respirator including an embodiment of an air-purifying device according to the present invention, in use.
Figure 2:
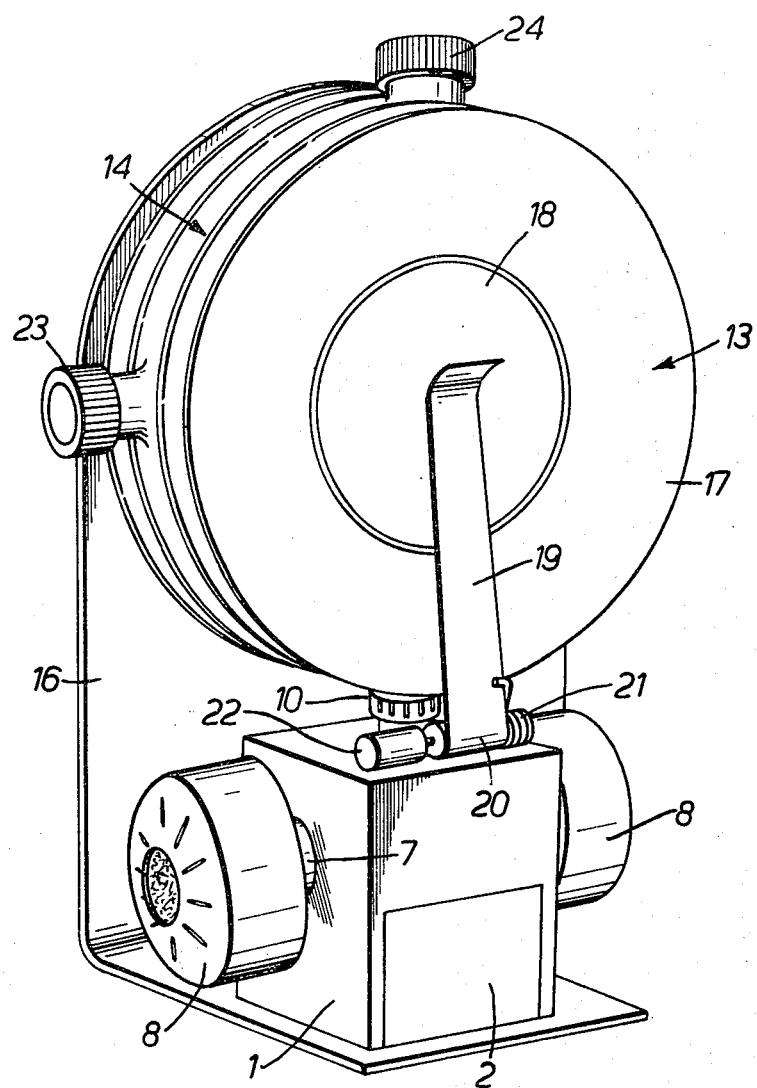
FIG. 2 is a perspective view of the air-purifying device shown in FIG. 1.
Figures 3, 4:
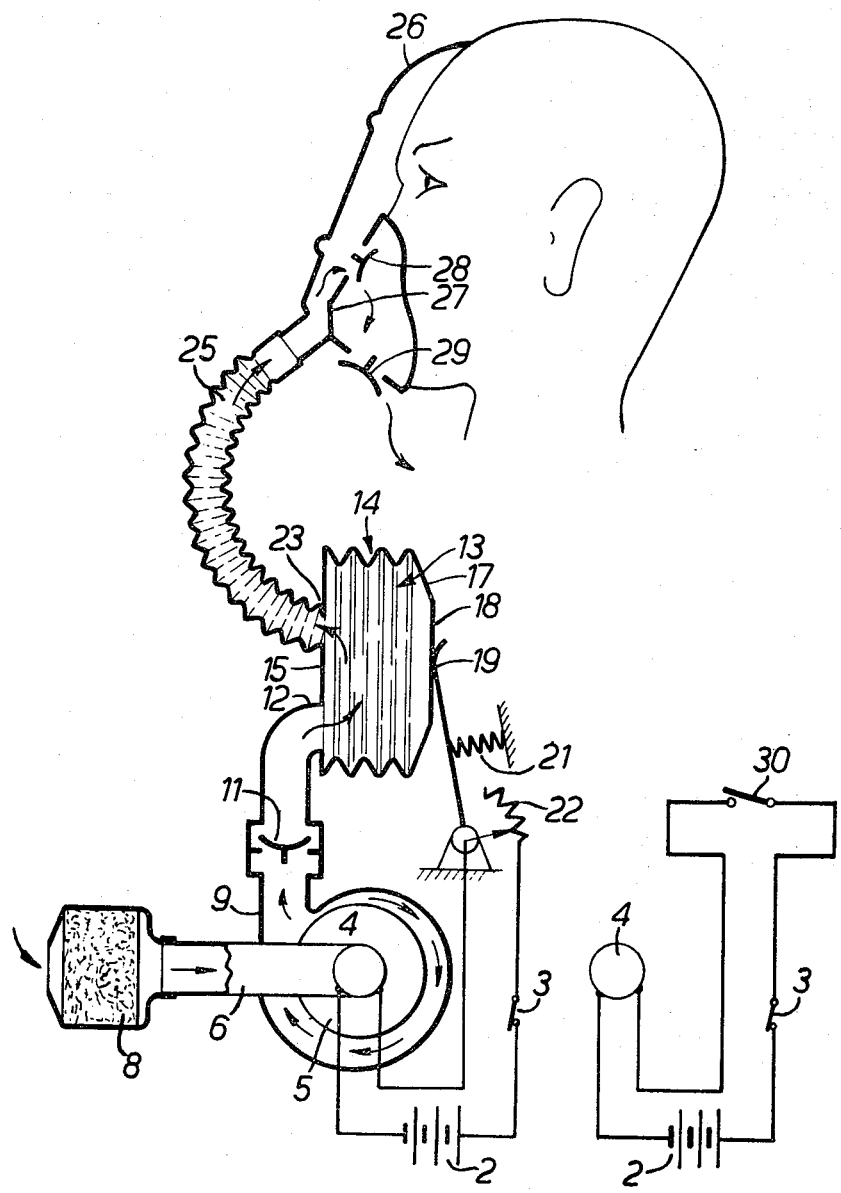
FIG. 3 is a diagrammatic sectional view of the respirator of FIG. 1 including the air-purifying device of FIG. 2.
FIG. 4 is a diagrammatic view of a modification of the respirator of FIG. 3.

The air-purifying device shown in FIGS. 1 to 3 of the drawings comprises a conventional pump unit 1 comprising a battery 2 which is connected by an on/off switch 3 to drive a motor 4 which in turn drives a fan unit 5 the inlet 6 of which is connected to two screw threaded air inlet conduits 7 into each of which are screwed two filters, as shown in the form of canisters 8 both of which make gas tight seals at the inlet conduit 7. The outlet 9 of the fan communicates with an outlet 10 of the unit at the top of the unit which is provided with a check or one-way valve 11 and is connected to the inlet 12 of an expandable breathing chamber which, as shown, has the form of a collapsible bag 13. The bag 13 is generally cylindrical with a circular section and has a convoluted periphery 14 so that it can expand and collapse in concertina fashion. One end wall 15 of the bag 13 is mounted on a support 16 also supporting unit 1 and the other end wall 17 is reinforced with a metal or synthetic plastic plate 18 against which an arm 19 bears. Arm 19 is pivoted at its lower end 20 and biased by a coil spring 21 so that the arm bears against and exerts a force on the bag in a direction to collapse it so as to maintain a constant pressure on air in the bag.

A rotary potentiometer 22 is associated with the arm pivot to be actuated by pivotal movement of the arm. The potentiometer 22 is connected in the power supply circuit for the motor which includes the battery and the off/on switch, to vary the voltage supplied to the motor so that movement of the arm results in a change in the voltage of the power supplied to the motor to speed up or slow down the motor and therefore the fan. The potentiometer is arranged so that, as the bag 13 is inflated by the fan, the voltage is decreased and therefore the motor and fan slow down, as the bag is deflated by the wearer drawing on the contents, the voltage is increased and the motor and fan speed up. To prevent over-inflation of the bag, the point of maximum inflation is determined by a mechanical stop (not shown) on the arm and an electrical cut-out is provided operated by a micro-switch (not shown) to cut off the power supply to the motor when the bag is at its point of maximum inflation. As soon as inflation of the bag drops below its maximum, the microswitch will close to reconnect the motor to the battery.

The bag 13 has alternative outlets 23 and 24 for coupling to a breathing hose (not shown in FIG. 2) which may be a long hose 25 connected to outlet 23 as shown in FIGS. 1 and 3 if the unit is worn on the back of the wearer (as shown) or a shorter hose connected to outlet 24 if the unit is to be chest mounted.

As shown the hose is connected to a full-face mask 26 with an inner mask 27 and which are provided with conventional inhalation and exhalation valves 28, 29, the exhalation valve having a relatively low resistance of approximately 128 pascals, as conventionally used in facepieces designed for use with positive pressure breathing.

In use, air is maintained in the face mask at a positive pressure equal to or less than the resistance of the exhale valve 29 by the pressure of arm 19 on the bag 13, the bias provided by spring 21 being adjusted accordingly. The pump is powerful enough to inflate the bag 13 against the bias of the arm 19 but not so powerful as to overcome the resistance of the exhale valve 29 in the face mask. Thus when the wearer is resting or breathing lightly, the pump will inflate the bag to its fully inflated position and will then be switched off by operation of the micro-switch. As soon as the inflation of the bag drops below its fully inflated condition, the microswitch will be closed and the inflation of the bag will be controlled via the potentiometer 22.

Blow-back through the pump and filters is prevented by the check valve 11. Additionally it is important to so arrange the working pressures of the exhale valve 29 in the face mask and the pressure generated in the bag by the biased arm 19 that the device does not go on to constant flow, but the pressure within the face mask always remains positive. To reduce over-run, the motor and fan inertias are reduced to a minimum.

In the unlikely event of pump failure, the wearer can breath through the canisters although with high inflation resistance. Additionally complete collapse of the bag 13 is prevented by internal supports (not shown) so that the wearer can breath through the canisters and complete collapse of the bag is prevented from sealing the system.

Preferably the canisters 8 are known gas and/or vapour and/or particulate material filter canisters/cartridges of the type normally screwed directly to a face mask although they may be of any other suitable type.

It will be appreciated that while the invention has particular application in relation to gas and vapour filtering, it is equally applicable to particulate material filtering because in either system an increase in the effective usage of the filter is beneficial.

While as shown in FIGS. 1 and 3, the air-purifying device of FIG. 2 is connected to a face mask covering only the nose and mouth of the wearer, it will be appreciated that the device can equally be used with a suitably valved and sealed positive pressure type helmet or hood which includes a facepiece and covers the entire head of the wearer.

Additionally, while as described the state of expansion of the bag is sensed and used to vary the voltage supplied to the pump unit, the potentiometer 22 may, as diagrammatically shown in FIG. 4, be replaced by switch means 30 which is operated by the arm 19 to connect the motor 4 to the battery 2 when the bag has reached a predetermined state of partial deflation and to disconnect the motor 4 from the battery when the bag is substantially fully inflated. Provision of switch 30 then avoids the need for a micro-switch to prevent over-inflation of the bag.

By appropriate design of the expandable bag 13 and its controls for the fan motor, it may be provided as an 'add-on' unit for existing positive pressure power assisted respirators, the bag simply being connected between the existing fan outlet and the hose connection to the facepiece, to enable existing respirators to be used for gas and/or vapour filtering economically.

In a further modification, the arm 19 may be omitted and the bag biassed to its collapsed condition by e.g. a helical spring, which may be arranged within the bag between the end walls 15, 17, or externally of the bag bearing against the end wall 15 and a mounting member extending parallel to member 16. The switch 30 is then arranged to be contacted by the end wall 15 or a member moving therewith when the bag is full inflated to disconnect the motor from the battery, and to reconnect the motor to the battery as soon as the state of inflation of the bag drops below full inflatation. The contact of switch 30 thus serves to sense the degree of expansion or inflation of the bag and the switch serves to control the power supplied to the pump means in dependence on the state of expansion of the bag.

What is claimed is:

1. An air-purifying device for attachment to a facepiece of the positive pressure type for providing purified air to the wearer of the facepiece, said air-purifying device comprising:
   (a) electrically powered pump means for pumping air, said pump means including inlet means and outlet means;
   (b) means connecting said pump means to a source of electrical power and including means for varying the power supplied from said power source to said pump means;
   (c) means for removing contaminants in the air;
   (d) means connecting said contaminant removing means to said pump inlet;
   (e) means defining an expandable chamber having an inlet and an outlet;
   (f) means biasing said expandable chamber towards a collapsed condition for maintaining a positive pressure in said chamber;
   (g) means connecting said chamber inlet with said pump outlet;
   (h) means adapted to connect said chamber outlet to a facepiece;
   (i) sensing means for sensing the degree of expansion of said expandable chamber; and
   (j) means connecting said sensing means with said power varying means for varying the power supplied to said pump means in dependence on the state of expansion of said expandable chamber.

2. A device as claimed in claim 1, wherein said expandable chamber comprises a bag which is generally cylindrical with a convoluted cylindrical wall.

3. A device as claimed in claim 1, wherein said sensing means comprises a pivotally mounted arm which bears against a wall of said expandable chamber, which wall in use moves in dependence on the state of expansion of said expandable chamber.

4. A device as claimed in claim 3, wherein said arm is connected to said means for varying the power supplied to said pump means in dependence on the angular position of said arm.

5. A device as claimed in claim 3, wherein said means for biasing said expandable chamber towards a collapsed condition for maintaining a positive pressure in said chamber comprises a spring acting on said arm.

6. A device as claimed in either claim 1 or claim 4, wherein said means for varying the power supplied comprise switch means.

7. A device as claimed in claim 6, wherein said switch means is arranged to be opened when said expandable chamber is substantially fully inflated for disconnecting said pump means from the power supply therefor and closed when said expandable chamber is partially deflated for connecting said pump means to the power supply.

8. A device as claimed in either claim 1 or claim 4, wherein said means for varying the power supplied comprises means for varying the voltage of the power supplied to said pump means.

9. A device as claimed in claim 8, wherein said means for varying the voltage comprise a rotary potentiometer mechanically coupled to said arm for angular movement therewith.

10. A device as claimed in claim 8, including switch means operable by said arm for disconnecting said pump means from the power supply when said expandable chamber is fully inflated.

11. A respirator of the positive pressure type including an air purifying device as claimed in claim 1.

* * * * *